United States Patent [19]

Song

[11] 4,224,765
[45] Sep. 30, 1980

[54] PLANT CULTURE CONTAINER

[76] Inventor: John S. Song, 2827 Sheridan Pl., Evanston, Ill. 60201

[21] Appl. No.: 10,088

[22] Filed: Feb. 7, 1979

[51] Int. Cl.³ .............................................. A01G 9/02
[52] U.S. Cl. ........................................... 47/85; 47/66; 220/22; 220/326; 220/371; 220/375
[58] Field of Search ..................... 47/85, 66; 220/375, 220/371, 326, 22, 21

[56] References Cited

U.S. PATENT DOCUMENTS

| | | | |
|---|---|---|---|
| 3,104,903 | 9/1963 | Futch et al. | 220/326 X |
| 3,240,378 | 3/1966 | Fox | 220/21 |
| 3,883,030 | 5/1975 | Mathews et al. | 220/375 X |
| 3,904,073 | 9/1975 | Schaefer et al. | 220/326 X |

FOREIGN PATENT DOCUMENTS

| | | | |
|---|---|---|---|
| 92975 | 11/1968 | France | 220/371 |
| 2362580 | 3/1978 | France | 47/85 |
| 156981 | 6/1978 | Netherlands | 220/375 |

*Primary Examiner*—Steven A. Bratlie
*Attorney, Agent, or Firm*—Darbo & Vandenburgh

[57] ABSTRACT

A partitioning insert is removably received in the base member of the container. The partitioning walls are larger at the top than at the bottom and terminate in posts which support the remainder of the partitions above the bottom of the container. The top of the container has a stepped flange which rests on and fits about the walls of the bottom of the container. At one end is a releasable latch and at the other is an interengagement between the two members. A part of the top of the container is at a lesser elevation than the remainder and has a vent opening, an air filter and a removable cover assembly.

7 Claims, 8 Drawing Figures

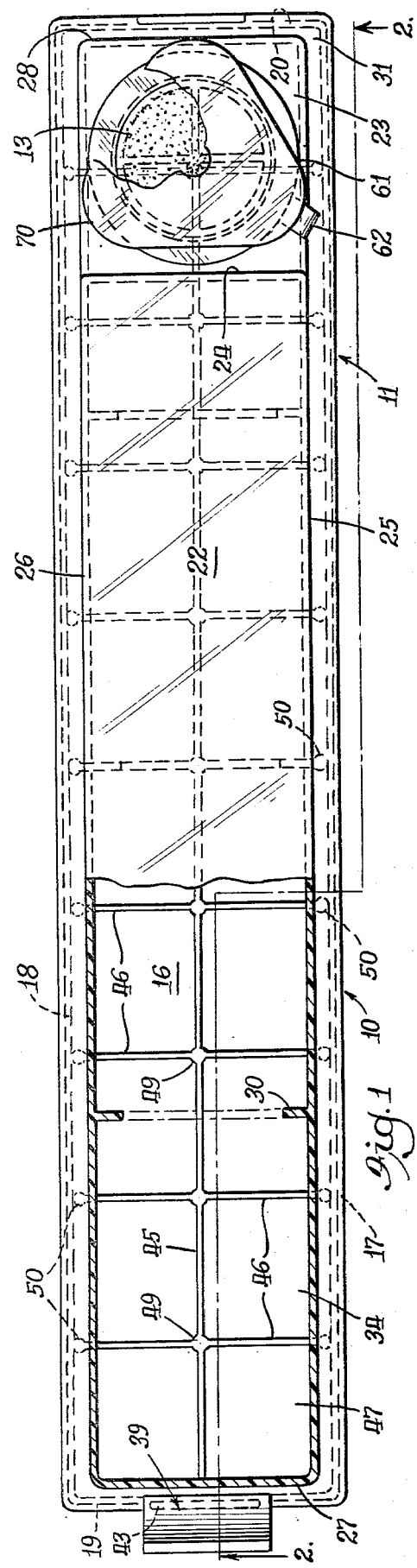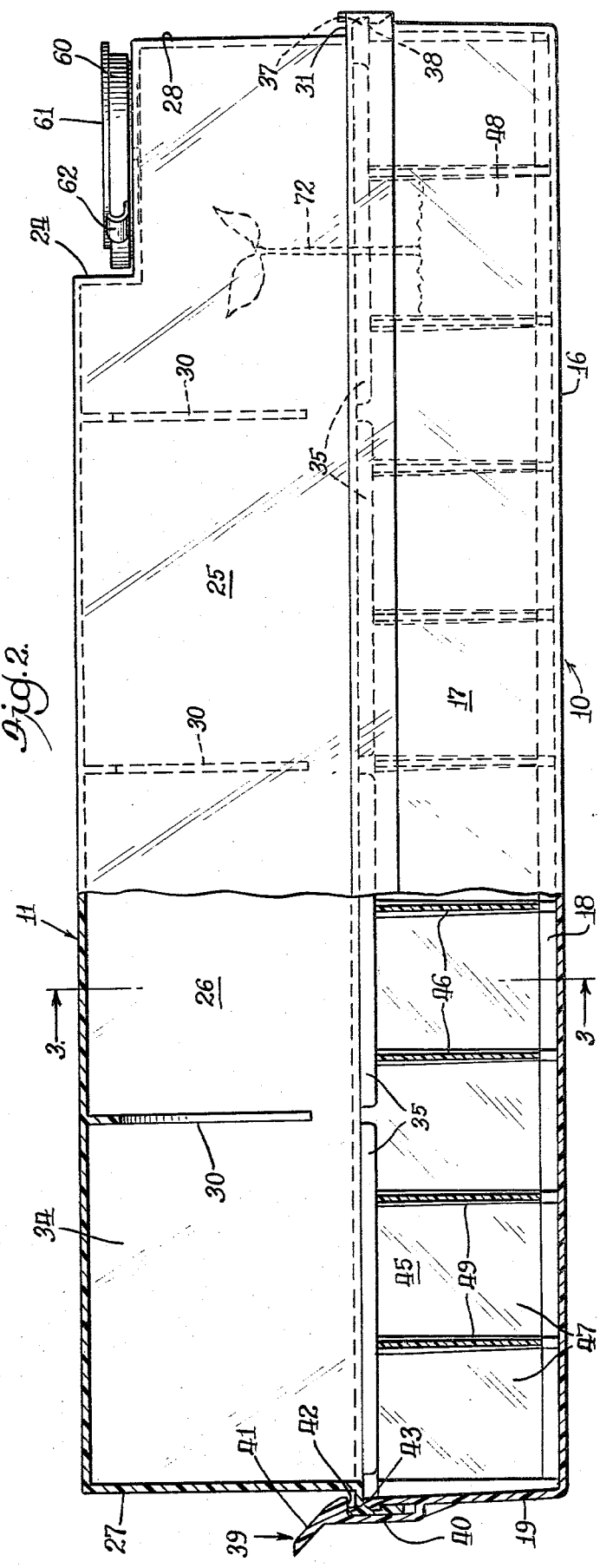

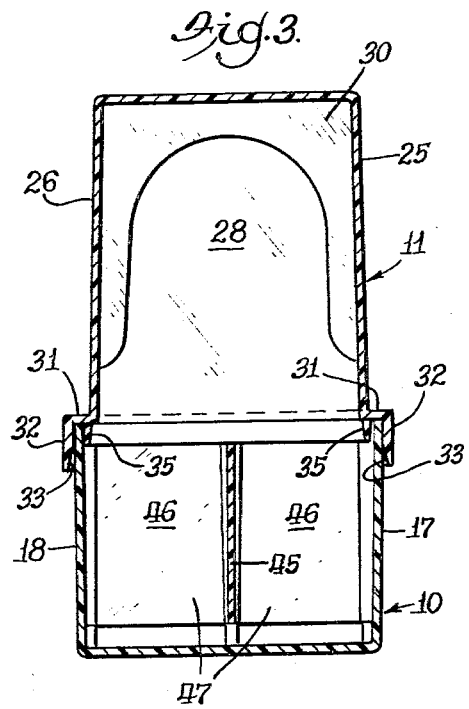
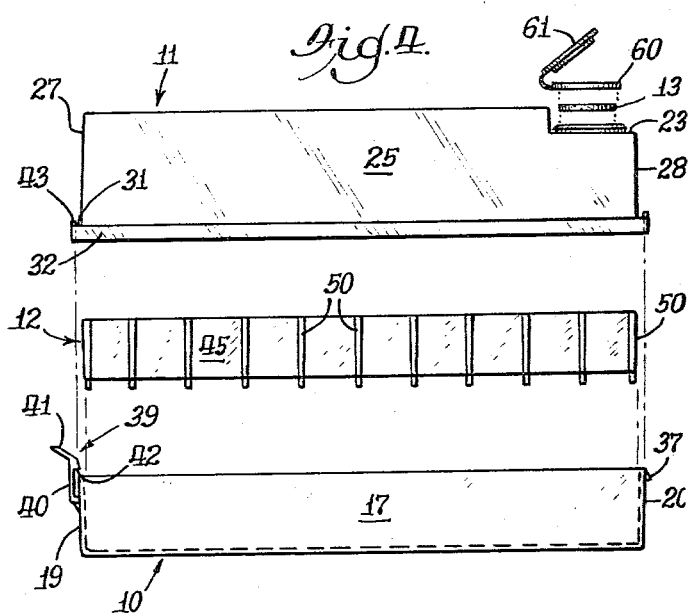
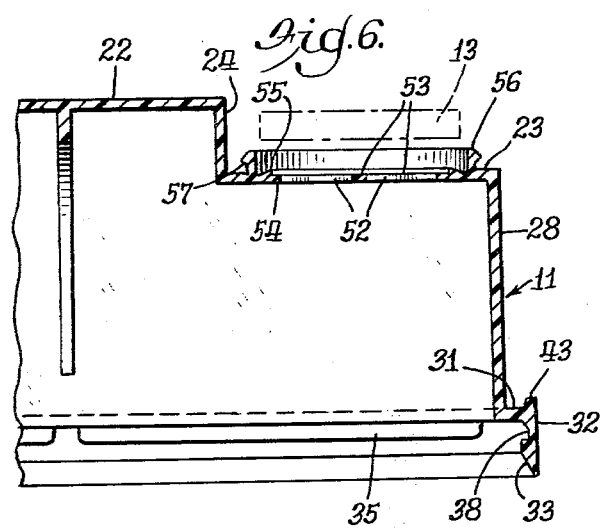
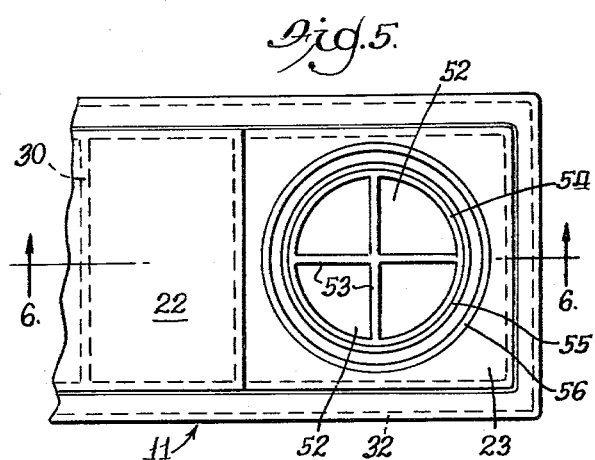
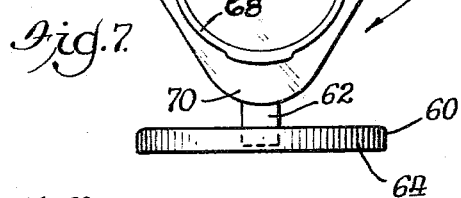
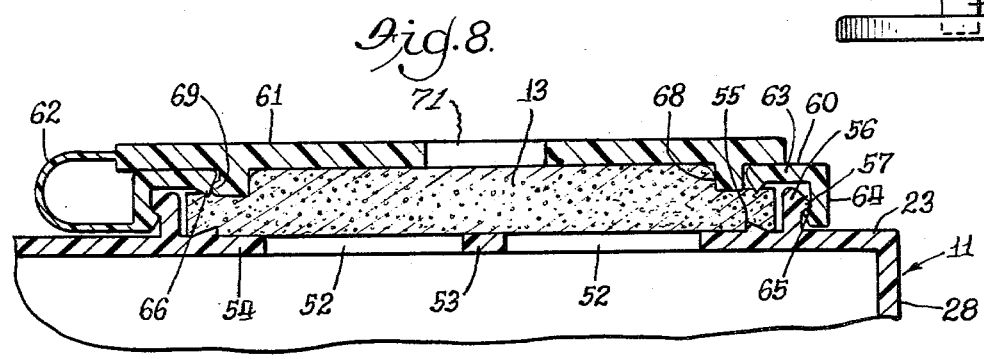

PLANT CULTURE CONTAINER

BACKGROUND AND SUMMARY OF THE INVENTION

Plant tissue cultures, e.g., plant tissue, parts of plants or plants, are grown under aseptic conditions. Some sort of a container is employed to maintain the aseptic condition. However, since air is necessary the container must be vented. The vent is provided with a filter so as to maintain the aseptic condition within the container. A very simple such container would be a test tube with a wad of cotton closing the open end and serving as a filter and, perhaps, a removable cap for the open end of the test tube. Other more sophisticated containers have been suggested, and to some extent used.

The principal object of the present invention is to provide such a culture vessel which is relatively simple and inexpensive to manufacture and which is almost foolproof so far as its use is concerned; that is, its construction is such that there is almost no opportunity for its misuse in a manner such that the desired condition would not be maintained within the vessel when it is used. It has the advantages that: the cover of the vessel is securely locked in place against accidental displacement; the members of the container are readily cleaned and/or sterilized for reuse; even when in use the containers may be stacked one upon the other without any functional impairment so far as their use is concerned; and the air filter is securely held in place against accidental displacement. Further objects and advantages of the invention will be apparent to those workers in the art from the following description taken in conjunction with the drawings.

Embodiments of the invention comprise top and bottom members defining an enclosed space for the culturing operation. These members are rectangular in horizontal cross section and elongated in one direction. At one of the narrow ends there is a releasable latch and at the other end a detent engagement. The bottom of the walls of the top member have an angular flange which seats on the top of the walls of the bottom member and fits about the outside of the bottom member walls. Along the elongated sides thereof are inner projections in juxtaposition to the tops of the bottom member walls. Thus those elongated walls of the two members are locked against displacement with respect to each other. The top is horizontal and has a depressed section at one end. In that depressed section is the vent opening with portions across the vent opening to support the air filter in that opening. The cover assembly for the vent opening includes a mounting ring engaging an annulus on the top about the vent opening. A strap hinge connects that ring to the cap. The mounting ring aids in holding the air filter.

DESCRIPTION OF THE DRAWINGS

FIG. 1 is a plan view of an embodiment of the invention, with portions broken away;

FIG. 2 is a section as seen at line 2—2 of FIG. 1;

FIG. 3 is a section taken at line 3—3 of FIG. 2;

FIG. 4 is an exploded view showing the components of the embodiment of FIG. 1;

FIG. 5 is a plan view of a part of the cover member in the area of the vent opening, with the cap and filter for that opening removed;

FIG. 6 is a section as seen at line 6—6 of FIG. 5;

FIG. 7 is an elevational view of the cap for the vent opening; and

FIG. 8 is an enlarged sectional view of the part of the cover member at the vent opening with the air filter and cap in place.

DESCRIPTION OF SPECIFIC EMBODIMENT

The following disclosure is offered for public dissemination in return for the grant of a patent. Although it is detailed to ensure adequacy and aid understanding, this is not intended to prejudice that purpose of a patent which is to cover each new inventive concept therein no matter how others may later disguise it by variations in form or additions or further improvements.

The individual components that make up an embodiment of the present invention are best seen in FIG. 4. There are a base member, generally 10, a top or cover member, generally 11, a partitioning member, generally 12, a filter 13 for the vent opening and a cover assembly, generally 14, for the vent opening.

The base member 10 comprises a bottom 16 and substantially vertical side walls 17 and 18 and end walls 19 and 20 integral therewith. The top of the top member comprises a horizontal, large portion 22 and a small portion 23 interconnected by a step 24. Depending from that top are substantially vertical side walls 25 and 26 and end walls 27 and 28. Within the top are reinforcing ribs 30 which are integral with the top and the side walls. As best seen in FIG. 3, the inner edge of these ribs is generally in the form of an inverted "U".

Along the bottom, distal ends of the walls of the top member 11, is an angular flange formed by a horizontal section 31 and a generally vertical section 32. The horizontal section seats on the top, distal ends of the walls of the bottom member 10. The vertical section fits snugly against the top area of those walls and has a tapered distal end, as seen at 33 (FIGS. 3 and 6), to facilitate fitting the two members together. This angular flange serves the dual purpose of supporting the top member on the base member and effectively providing a fluid-tight seal between the two members to prevent contamination from getting into the culture space 34 within the members, through the juncture between the two members. Along the side walls only, the angular flange has downwardly extending projections 35 (FIGS. 2, 3 and 6), which extend immediately inside of the top portions of the side walls of the bottom member. Thus the side walls of the two members are locked together, so far as transverse displacement is concerned, by the side walls of the bottom member being trapped between projections 35 and vertical sections 32.

At end wall 20 of the bottom member there is a projection 37 adjacent the top thereof to engage in recess 38 of the angular flange of the top member. There is a corresponding recess 38 at the other end of the top member so that the top member can be put on the base member in either orientation. At the other end the two members are interconnected by a releasable latch, generally 39. This is formed by a somewhat flexible arm 40 integral with end wall 19 at its bottom end and having a finger grip 41 at its distal end. Intermediate the ends the arm defines an abutment 42 which fits over the raised abutment 43 on the horizontal section 31. Again, there is a corresponding abutment on the other end of the top member.

The partition member 12 includes a longitudinal partition wall 45 and a plurality of transverse partition walls 46. As best seen in FIGS. 2 and 3, these partition walls are thicker at the top than at the bottom; thus the compartments 47 which are defined by the walls, and the walls of the bottom member 10, are smaller at the top than they are at the bottom. This aids in holding the planting medium 48 in the compartments. At the juncture of the partition walls there are enlargements 49 and at the distal ends of the partition walls are enlargements 50, all of which enlargements form posts. These posts extend below the level of the partition walls whereby the partition walls are supported above the level of bottom 16. This permits liquid to migrate along the bottom of the base member.

In the small portion 23 of the top is a ventilation opening 52. Bars 53 extend across this opening. Immediately externally of the opening is a flat circular portion 54 and then a peaked annular ridge 55. A short distance outside this ridge is an upstanding annulus 56 which has an outwardly annular projection 57. The filter 13 fits within annulus 56 and is centered thereby over the opening 52. The filter is supported by the circular portion 54 and the bars 53 which prevent it from going through the opening. The peaked annular ridge 55 bites into the filter 13 and prevents air from leaking down about the sides and bottom thereof to and from the opening 52.

The cover assembly 14 comprises a mounting ring 60, a cap 61 and a strap 62 interconnecting the ring and the cap. The three are molded integrally of plastic, sufficiently flexible that the strap 62 forms a hinge. The mounting ring comprises a top annular plate 63 and a side annular plate 64. The side annular plate has an inward projection 65 which engages below the outward projection 57. The top annular plate 63 has a downwardly extending, peaked, annular projection 66 which bites into the filter 13, again to prevent air leakage about the filter. The cap 61 has a downwardly extending annulus 68 which has three projections 69. It will be noted in FIG. 7 that the cap 61 is of generally triangular configuration, with three outwardly extending ears 70, and that projectons 69 are correspondingly arranged. The outwardly extending ears provide a place for the fingers of a person to grasp the cap to disengage it from the mounting ring 60 when the cap is in the closed position (FIG. 8). Due to atmospheric pressure changes the container wants to breathe. Thus an opening 71 is provided in the cap so that such breathing will take place through the filter 13 when the cap is in place.

The members 10, 11 and 12 are molded from a plastic. The walls are sufficiently thick to maintain the desired form and not seriously bend when grasped, etc. For example, walls 17, 18, 19, 20 are 0.062 inches (1.575 mm), and walls 25–28 are 0.055 inches (1.397 mm) thick. The top 22 and the bottom 16 are 0.062 inches (1.575 mm) thick. The plastic employed is polypropylene, the clearest available of such material. It has a somewhat cloudy appearance, but is sufficiently transparent so that one can see what is within the container and to transmit the light rays suitable for growth. Preferably, the filter 13 is an open-cell cellular plastic material having one hundred pores per inch.

To a worker in the art, no explanation of the manner of use is necessary. With the cover removed, and the partition member present in the base member, the compartments 47 are filled with a growth medium. A typical medium consists of agar (a jelling material), water, hormone and plant food. When hot it is a liquid and is poured into the base member. At room temperature it becomes a gel. A plant cell is put into the medium in each compartment. The top member is then placed on the bottom member. Presumably at this stage the filter is in place. It is held by the mounting ring 60. In time the plant cells grow to plant size, e.g., plant 72. During the initial part of the cultivation of the plants, no supplemental air normally is required so that the cap 61 is fastened down in the position illustrated in FIG. 8. Later in the growing period the cap will be moved to an open position to permit additional air to enter the container through filter 13. To conserve space, the containers may be stacked on top of each other, even during plant culturing. Thus an upper container will rest upon the large portion 22 of the top of the next lower container. As compared to a group of test tubes, which must be held in a rack, embodiments of the present invention use significantly less space. Each compartment serves the purpose of one test tube. Embodiments may be made in various sizes, and with various numbers of compartments, as required. The components are all autoclavable and thus reusable.

I claim:

1. A container for use in culturing plants in a growth medium, said container comprising a base member having a rectangular bottom and four, substantially vertical walls extending upwardly from the bottom, a top member having a top and four, substantially vertical walls extending downwardly from the top with the distal ends thereof in juxtaposition to the distal ends of the walls of the base member, one of said members having means at the distal ends of the walls thereof and engaging the distal ends of the walls of the other member and supporting the top member on the base member and forming substantially a fluid-tight seal therebetween, said members defining an enclosed space within which said plants may be cultured with part of that space within the base member for holding said medium, the top member having a vent opening therein communicating with said space and the exterior of said container and removable cover means for said vent opening, an air filter mounted on the top member and across said opening, and a removable insert within said part of said space and subdividing that part of the space into a plurality of compartments, said insert being formed by a plurality of partitions having tops and bottoms, said partitions being thicker at the tops thereof than at the bottoms whereby said compartments are smaller at the tops than at the bottoms, some of said partitions having distal ends in juxtaposition to the walls of the base member, each of said distal ends being larger in transverse cross section than is the remainder of the partition thereby forming posts, said posts extending below the remainder of the partitions whereby there is a space below the remainder of the partitions through which liquid can flow.

2. A container as set forth in claim 1,
wherein two of said walls of each member are sides and are substantially longer than the remaining two walls which are ends, said member having means being the top member and that means including downwardly projections fitting about the distal ends of the side walls of the base member to align the side walls of the two members, at one of said ends that means having a wall in juxtaposition to the end wall of the base member and with a recess therein, that end wall of the base member having a protrusion extending into said recess; and including releasable latch means interconnecting the members at the end thereof opposite said protrusion and recess.

3. A container as set forth in claim 2, including a plurality of reinforcing ribs between the top and the side walls of the top member, each of said ribs having a lower edge having the shape of an inverted "U" centered between the side walls of the top member.

4. A container as set forth in claim 3, wherein said top has a portion that is relatively short in relation to the length of the remainder of the top, the remainder of the top being generally in a horizontal plane, said opening being in said short portion, said short portion being at an elevation such that the cover is below said plane when in place covering said opening.

5. A container for use in culturing plants in a growth medium, said container comprising a base member having a rectangular bottom and four, substantially vertical walls extending upwardly from the bottom, a top member having a top and four, substantially vertical walls extending downwardly from the top with the distal ends thereof in juxtaposition to the distal ends of the walls of the base member, one of said members having means at the distal ends of the walls thereof and engaging the distal ends of the walls of the other member and supporting the top member on the base member and forming substantially a fluid-tight seal therebetween, said members defining an enclosed space within which said plants may be cultured with part of that space within the base member for holding said medium, the top member having a vent opening therein communicating with said space and the exterior of said container and removable cover means for said vent opening, an air filter mounted on the top member and across said opening, and a removable insert within said part of said space and subdividing that part of the space into a plurality of compartments, said top having a portion that is relatively small in relation to the size of the remainder of the top, the remainder of the top being generally in a horizontal plane, said opening being in said small portion, said small portion being at an elevation such that the cover is below said plane when in place covering said opening.

6. A container as set forth in claim 5, wherein
said top includes an upstanding annulus about said opening, said filter being within said annulus, said top including means for supporting the filter and preventing the filter from being displaced downwardly through the opening, and
said cover means includes a mounting ring, a cap and a flexible strap connecting the cap and ring and forming a hinge, said mounting ring frictionally engaging said annulus, said cap and ring having releasable interengaging means for holding the cap onto the ring to close off the ring and prevent air from the outside to flow into said space and vice versa, said ring having means for holding the filter against upward displacement away from its position over the opening.

7. A container as set forth in claim 6, wherein
said top has a peaked annulus extending upwardly within said upstanding annulus and concentric therewith, and
said mounting ring includes a top annular plate and a peaked annulus extending downwardly from the annular plate,
said peaked annuli projecting into said filter.

* * * * *